United States Patent [19]

Ishii et al.

[11] Patent Number: 5,393,742
[45] Date of Patent: Feb. 28, 1995

[54] PREPARATION FOR TREATING RENAL DISEASE

[75] Inventors: Takayuki Ishii; Makiko Kasano; Tae Yasunaga; Mariko Ishii; Mamoru Sugimoto; Kenkichi Tomita, all of Tokyo; Takeshi Miyata, Kumamoto; Makoto Tanaka, Tokyo, all of Japan

[73] Assignee: MECT Corporation, Tokyo, Japan

[21] Appl. No.: 109,614

[22] Filed: Aug. 19, 1993

Related U.S. Application Data

[63] Continuation-in-part of Ser. No. 751,150, Aug. 28, 1991, abandoned.

[30] Foreign Application Priority Data

Aug. 30, 1990 [JP] Japan .................. 2-229315

[51] Int. Cl.$^6$ ............................... A61K 31/70
[52] U.S. Cl. ................................ 514/23; 514/62
[58] Field of Search .............. 514/23, 62; 536/55.2, 536/119

[56] References Cited

U.S. PATENT DOCUMENTS

| | | |
|---|---|---|
| 3,896,228 | 7/1975 | Richardson . |
| 4,122,189 | 10/1978 | Kurosawa et al. . |
| 4,178,285 | 12/1979 | Felts et al. . |
| 4,264,589 | 4/1981 | Felts et al. . |
| 4,339,442 | 7/1982 | Takemoto et al. . |
| 4,410,515 | 10/1983 | Holick et al. . |
| 4,442,093 | 4/1984 | Maeda et al. . |
| 4,521,410 | 6/1985 | Holick et al. . |
| 4,661,294 | 4/1987 | Holick et al. . |
| 4,698,332 | 10/1987 | Ogasawara et al. . |
| 4,820,689 | 4/1989 | Ikuzawa et al. . |
| 4,912,215 | 3/1990 | Yazawa et al. . |
| 5,008,243 | 4/1991 | Ikuzawa et al. . |
| 5,177,062 | 1/1993 | Miyata et al. . |
| 5,182,266 | 1/1993 | Kleinert . |

FOREIGN PATENT DOCUMENTS

| | | |
|---|---|---|
| 0296620 | 12/1988 | European Pat. Off. . |
| 0386657 | 9/1990 | European Pat. Off. . |
| 1299294 | 4/1989 | Japan . |

OTHER PUBLICATIONS

Hirsch et al., Host Modification . . . , Journal of Immunology, vol. 127, No. 5, Nov. 1981.
Gorog et al., Anti-Inflammatory Effect . . . , Agents and Actions, vol. 8/5, 1978.
Itoh, Chemical, Pharmacological and Biochemical Confirmation . . . , Yakuri to Chiryo, vol. 13, No. 7, Jul. 1985.
Murata et al., Antiallergic Action . . . , 61st Gen. Conference, Mar. 23–26, 1977.
Messina, Glomerular Epithelial Abnormalities . . . , vol. 126, No. 2.
Kerjaschki, Reduced Sialylation of Polocalyxin . . . , AJP, Mar. 1985.
Kasinath et al., Effect of Puromycin, pp. F590–F596, 1988.
Olson et al., Alterations in the Charge and Size Selectivity . . . , Laboratory Investigation, vol. 44, No. 3, 1981.
Baricos et al., Characterization in Normal Rat Kidney . . . , Biochem., 1986, 239, 705–710.
Diamond, Irreversible Tubulointerstitial Damage . . . , American Journal of Pathology, vol. 137, No. 6, Dec. 1990.
Williams & Wilkins, Stedman's Medical Dictionary, 24th Edition, pp. 932 & 934.

Primary Examiner—Ronald W. Griffin
Assistant Examiner—Everett White
Attorney, Agent, or Firm—McGlew & Tuttle

[57] ABSTRACT

A preparation is useful for treating renal disease, such as nephritis and especially nephrosis (nephrotic syndrome), which comprises an effective amount of N-acetylneuraminic acid shown by the formula $$\left[ \begin{array}{c} \text{HO} \diagup \overset{\text{OH}}{\diagdown} \diagup \overset{}{\diagdown} \overset{\text{O}}{\diagdown} \diagup \overset{\text{OH}}{\diagdown} \text{COO} \\ \text{CH}_3\text{CO}-\text{HN} \diagdown \overset{\text{OH}}{\underset{\text{OH}}{\diagup}} \end{array} \right]_n \cdot [Z]$$

wherein, when n is 1, Z represents hydrogens, lithium, potassium, sodium, ammonium or organic ammonium, and when n is 2, Z represents calcium, barium or magnesium, and a pharmacologically acceptable carrier.

7 Claims, No Drawings

PREPARATION FOR TREATING RENAL DISEASE

CROSS REFERENCE TO RELATED APPLICATION

This is a continuation in part of U.S. application Ser. No. 751,150, filed Aug. 28, 1991, now abandoned.

BACKGROUND OF THE INVENTION

1. Field of the Invention

This invention relates to use of a preparation for therapeutically treating renal disease such as nephrotic syndrome (nephrosis), particularly glomerular nephrosis, the preparation containing N-acetylneuraminic acid (NANA) or its salt as an effective ingredient.

2. Description of the Prior Art

N-acetylneuraminic acid (NANA), which is a sialic acid, has been reported in the following articles [1] to [4] to exhibit anti vital action, anti inflammatory action and anti allergic action, as the case may be:

[1] Hirsch, R. L. et al, *The Journal of Immunology* 1981, 127 (No. 5):1740–1743 (anti vital action),

[2] Gorog, P. et al, *Agents and Actions* 1978, 8 (No. 5):543–545 (anti inflammatory effect),

[3] Itoh, H. et al, *Yakuri to Chiryo* (Japanese) 1985, 13 (No. 7):479–494 (anti inflammatory action),

[4] Murata, Y. et al, The 61st General Conference of Japan Pharmacology Society, March 23–26, 1988, Anti-allergic action of N-acetylneuraminic acid (NANA) in guinea pigs (Japanese), 0–276 English abstract.

The inducing mechanism of puromycin aminonucleoside (PAN) on nephrosis, i.e. nephrotic syndrome, is discussed in the following articles [5] to [10] regarding PAN induced nephrotic syndrome modeling studies:

[5] Messina, A. et al, *Am J Pathol* 1987, 126:220–229,

[6] Kerjaschki, D. et al, *Am J Pathol* 1985, 118:343–349,

[7] Kasinath, B. S. et al, *Am J Pathol* 1988, 225:F590–F596,

[8] Olson, J. L. et al, *Lab Invest* 1981, 44 (No. 3):271–279,

[9] Baricos, W. H. et al, *Biochem J* 1986, 239:705–710,

[10] Diamond, J. R. et al, *Am J Pathol* 1990, 137 (No. 6):1323.

These articles [5] to [10] make clear that nephrosis (nephritis) as induced by PAN is commonly referred to as nephrotic syndrome, and that such is regarded as comparable to nephrotic syndrome as actually occurs in human patients.

It is noted that Stedman's Medical Dictionary, 24th ed 1982, defines "nephritis" (p. 932) as "Inflammation of the kidneys" and "nephrosis" (p. 934) as "1. Nephropathy. 2. Degeneration of renal tubular epithelium. 3. Nephrotic syndrome" whereas "lipoid n[ephrosis]" is defined (p. 932) as "membranous glomerulonephritis." This interchangeability of "nephrosis" and "nephritis" as used in "lipid nephrosis" and its equivalent "membranous glomerulonephritis," is also observed in referring to PAN induced nephritis and PAN induced nephrosis as contemplating nephrotic syndrome.

5] Messina, A. et al points to glomerular epithelial abnormalities as the mechanism of PAN induced nephrosis (nephrotic syndrome) which causes proteinuria (albuminuria). It refers to PAN induced proteinuria in aminonucleoside nephrosis experimental modeling and its applicability to human glomerular disease, particularly in minimal change disease (lipoid nephrosis, i.e. membrane glomerulonephritis), due to its many common features with minimal change disease. Its findings on rats indicate that in PAN nephrosis, proteinuria results from glomerular epithelial injury, leading to formation of focal gaps in the epithelial covering of the glomerular basement membrane (GBM), where increased water flux causes plasma proteins to be dragged across the GBM filter to the urinary space.

Because such focal areas of externally denuded GBM have been observed in the glomeruli of nephrotic (human) patients with various types of glomerulonephritis, including focal glomerulosclerosis and hyalinosis, amyloidosis, minimal change disease, membranous glomerulonephritis (lipid nephrosis), diabetic glomerulopathy, and lupus nephritis, it is considered that formation of these bare areas of GBM also play a role in the pathogenesis of proteinuria in these (human) glomerular diseases.

This article exemplifies the equivalency or interchangeability of nephrosis and nephritis as regards nephrotic patients with various types of glomerulonephritis, and the applicability of animal (rat) test results as indicative of comparable results in human patients suffering from renal disease.

[6] Kerjaschki, D. et al shows that loss of polyanion, which is present on glomerular epithelial cells (GEC), occurs in PAN nephrosis. It notes that minimum change nephrosis is a disease that can be induced experimentally in rats by PAN, and that proteinuria is the pathophysiologic hallmark of minimum change nephrosis both in PAN rats and in humans. It indicates that rat renal GEC (podocytes) contain glomerular epithelial polyanion which is lost in minimum change nephrosis, e.g. as induced in rats by PAN.

This article exemplifies the identity of proteinuria as associated with both animal (rat) and human minimum change nephrosis.

[7] Kasinath, B. S. et al shows that PAN reduces heparan sulfate proteoglycan (HSPG) in rat GEC. It notes the in vivo and in vitro toxicity of PAN to rat GEC in regard to PAN induced nephrosis.

[8] Olson, J. L. et al demonstrates that both glomerular size and charge barriers of GBM are impaired in PAN nephrosis. It notes that aminonucleoside nephrosis (proteinuria and renal damage) is an experimental model of nephrosis induced as a disease in rats by administering PAN, resulting in renal damage including GEC injury. It also notes that the mechanism of proteinuria in this model of nephrosis (nephrotic rats) has been frequently investigated, and that the aminonucleoside nephrosis induced in the rats provides a model comparable to the minimal change nephrotic syndrome in human patients.

This article similarly exemplifies the applicability of animal (rat) test results as indicative of comparable results in human patients suffering from renal disease.

[9] Baricos, W. H. et al indicates that normal glomeruli contain relatively high activity of neuraminidase, which activity is not changed by onset of proteinuria associated with PAN induced nephrotic syndrome. It refers to experimentally induced nephrotic syndrome in rats by PAN as a well documented model of glomerular disease, and compares human and experimental glomerular diseases interchangeably and also compares PAN models of glomerular nephritis and nephrotic syndrome interchangeably.

This article similarly exemplifies the equivalency or interchangeability of nephrosis and nephritis as regards glomerular nephritis and nephrotic syndrome, and the applicability of animal (rat) test results as indicative of comparable results in human patients suffering from renal disease.

[10] Diamond, J. R. et al refers to the role of dosage schedule and administration route of PAN in the progress of thereby induced proteinuria, noting that aminonucleoside nephrosis, i.e. in rats per PAN induced proteinuria, is an experimental model of nephrotic syndrome which, depending on the dosage and administration route, progresses to focal and segmented glomerulosclerosis (FSGS).

In essence, articles [5] to [10] collectively show that PAN induced nephrotic syndrome (PAN nephrosis, PAN nephritis) and associated proteinuria represent an experimental model in lower mammals (rats, guinea pigs, etc.) of glomerular disease (abnormality) in higher mammals (human beings), i.e. glomerular nephritis (and its equivalents: minimum change nephrotic syndrome, lipoid nephrosis, membranous glomerulonephritis, glomerular nephrosis, etc.), with the test results of therapeutic treatment of lower mammals being indicative of comparable results in human patients suffering from renal disease.

The following patents [11] to [20] relate to methods of treating renal disease:

[11] U.S. Pat. No. 3,896,228, issued Jul. 22, 1975 to Richardson, concerns treating nephrosis, i.e. nephropathies or chronic nephritis, by administering to an animal in need of such treatment a therapeutically effective amount of a prolactin inhibitor such as ergocornine, which thereby increases urine volume and pH (or urine electrolyte values, particularly sodium and potassium values). Tests on animals (rats) which normally suffer from nephrosis or a deposition of urine proteins (albumins and globulines) in kidney tubules indicate that such deposition is lowered following treatment, which is attributed to increased solubility of the urine proteins following prolactin inhibitor administration. The treatment can be used for conditions where protein deposits or casts already exist in the kidney tubules such as nephrosis or renal failure, especially chronic renal failure, whereby degenerative progression of renal failure may be inhibited in its early stages before complete blockage of kidney tubules occurs following urine protein deposition.

The prolactin inhibitor may be formulated with a carrier such as ascorbic acid, acetic acid, ethanol and water for solutions, and talc, lactose, maize starch, polyvinyl pyrrolidone and magnesium stearate for solid forms, and administered at a daily dose of about 0.01–3.0 mg/kg of animal body weight, or for larger mammals at a daily dose of about 0.5–15 mg. Parenteral unit dosage forms may contain about 1 mg of the inhibitor, and oral unit dosage forms may contain about 3 mg, or for larger mammals about 750–3000 mg.

This patent recognizes the equivalency or interchangeability of nephrosis and nephritis as regards chronic renal failure.

[12] U.S. Pat. No. 4,122,189, issued Oct. 24, 1978 to Kurosawa et al, concerns treating a human exhibiting a disorder of excessive urinary protein and/or of secondary hyper lipoidemia due to renal disease by internally administering to the human a known methyl methionine sulfonium salt in an amount effective to produce anti-excessive urinary protein therapy and/or anti-hyper lipoidemia therapy during the course of renal disease. It is noted that in therapy for renal diseases, certain agents have been used as medicines for nephrotic syndrome, and accordingly said sulfonium salt also serves as a medicine for renal disease nephrotic syndrome which is characterized by excessive urinary protein. The sulfonium salt is effective for excessive urinary protein, hypercholesterolemia, as clinical tests on patients suffering from excessive urinary protein (e.g. due to nephritis, nephrotic syndrome, etc.) indicate elimination or reduction of urine protein consequent said salt treatment.

Aminonucleoside nephrosis therapy tests on rats, in which aminonucleoside (AN) was used to induce renal disease, followed by treatment with the sulfonium salt, produced analogous results to those obtained in said clinical tests on patients. Hetero anti kidney serum (rabbit) nephritis therapy on rats, in which anti kidney serum was used to induce renal disease, followed by treatment with the sulfonium salt, also produced analogous results.

The sulfonium salt may be administered at a daily dosage of more than 200 mg, usually 1000–2000 mg in an oral dose form for adults, or in other medical forms.

This patent recognizes the equivalency or interchangeability of nephrosis and nephritis as regards nephrotic syndrome and nephritis renal disease, and establishes that induced renal disease test results on animals such as rats are indicative of comparable results in human patients suffering from renal disease.

[13] U.S. Pat. No. 4,178,285, issued Dec. 11, 1979, and its division [14] U.S. Pat. No. 4,264,589, issued Apr. 28, 1981, to Felts et al, commonly show the separating of the active alpha$_1$ acid glycoprotein (alpha$_1$ -AG) fraction, a co-factor in the lipoprotein lipase reaction, from nephrotic animal and human urine, for use in replacement therapy in an effective amount in nephrotic animals (rats) to reverse the defect in triglyceride (TG) removal caused by loss of plasma constituents in urine, i.e. to reduce the increased amount of TG in the blood. Rats with PAN induced nephrotic syndrome showed a decrease in TG (lipid) clearance, which was restored to normal by injection of said AG fraction, suggesting that elevated plasma TG in human nephrotic patients is the direct result of excessive loss of said AG fraction and/or associated components from plasma into urine and that human patients are amenable to replacement therapy.

As to nephrotic syndrome or kidney disease, it is stated that a severe excess of lipids in the blood is a common disorder in patients or experimental animals with kidney disease characterized by excess of protein in urine (proteinuria) and reduced protein in blood (hypoproteinemia), the elevated excess of TG in the blood being considered to result from a slower clearance of chylomicrons and very low density lipoproteins (VLDL) from the circulation, and/or increased VLDL synthesis by the liver. It is postulated that urinary loss of apolipoproteins and other co-factors necessary for TG clearance by the lipoprotein lipase (LPL) enzyme system is responsible for a defective clearance of chylomicrons and VLDL.

Per the teaching of these patents, an LPL co-factor in urine was identified which is similar or identical to plasma alpha$_1$ -AG and/or an associated component, and which in experimental nephrotic rats with a TG removal defect, can restore the TG metabolism rate to normal. This confirms that experimental nephrosis is induced in rats by administering PAN, whereby they display the common disorders of human nephrotic syndrome: proteinuria, hypoproteinemia and hypertriglyceridemia, the nephrotic rats specifically displaying a reduced rate of TG clearance which was reversed on administering said AG fraction such that TG clearance increased to the normal rate.

These patents similarly establish that induced renal disease test results in animals such as rats are indicative of comparable results in human patients suffering from renal disease.

[15] U.S. Pat. No. 4,339,442, issued Jul. 13, 1982 to Takemoto et al, concerns treating adrenal atrophy by administering to a host afflicted therewith a therapeutically effective amount of a stated gynosaponin, which is indicated to act on the cells of animals, including man. Clinical tests on a human patient having as a disease: chronic nephrosis type nephritis, and a moon face caused by glucocorticoid (steroid) administration, showed the effectiveness of treatment with said gynosaponin together with the glucocorticoid in improving kidney function (cols. 26-27).

The gynosaponin may be formulated with a solid or liquid excipient or carrier, e.g. as an internal (oral) preparation including lactose, starch, dextrin, calcium phosphate, calcium carbonate, etc., at a daily dosage in man (human being) of about 50–1000 mg.

This patent similarly recognizes the equivalency or interchangeability of nephrosis and nephritis as regards chronic nephrosis type nephritis.

[16] U.S. Pat. No. 4,442,093, issued Apr. 10, 1984 to Maeda et al, concerns treating hyper phosphatemia due to reduction of excreting function (increased resorption) in the kidneys in the morbid state such as that of chronic renal failure, hypo parathyroidism, acromegaly and acute dis-used bone atrophy by administering to a human or an animal suffering therefrom a therapeutically effective amount of a stated hydroxy cholecalciferol compound. Administering said compound to rats in a state of hyper phosphatemia due to nephrectomy (resulting in one third of a kidney remaining), as well as to rats pretreated with PAN (AN) to bring them to a stage of hyper phosphatemia, in each case caused reduction of the serum inorganic phosphate level of the rats. Administering said compound to a human patient having chronic renal failure showing a symptom of hyper phosphatemia, similarly caused reduction of the serum inorganic phosphate level of the patient to normal.

Said compound may be formulated with ethyl alcohol, isopropyl alcohol, ethylene glycol, propylene glycol solution, oil solution, aqueous suspension, etc. Triglyceride esters of fatty acids such as capric and caproic acids, corn oil, etc. may be used as solvent for the oil solution. Other formulation components include lactose, magnesium stearate, sorbic acid, sorbate salts, saccharides or their alcoholic derivatives, physiological saline solution, surfactants, anti oxidants, etc. The daily dose of said compound to an adult patient of 50–60 kg average body weight is about $1 \times 10^{-2}$ to $1 \times 10^5$ (0.001–100,000) micrograms (cols. 8–9).

This patent confirms that induced renal disease test results in animals such as rats are indicative of comparable results in human patients suffering from renal disease (cf. col. 5).

[17] U.S. Pat. No. 4,820,689, issued Apr. 1, 1989, and its division [18] U.S. Pat. No. 5,008,243, issued Apr. 16, 1991, to Ikuzawa et al, commonly concern treating nephrotic syndrome such as ameliorating proteinuria and proteinemia, by administering to a human suffering therefrom a therapeutically effective amount of a known stated glycoprotein compound. Tests of administering said compound to rats made to show nephrosis-like symptoms by administration of AN (aminonucleoside), which is known to cause proteinuria, and to a human patient having lupus nephritis as well as to a human patient having diabetic nephropathy, showed analogous effects for repressing proteinuria due to AN, or ameliorating lupus nephrosis or diabetic nephropathy (FIGS. 5–7; cols. 7 and 19–20).

Said compound may be formulated with conventional additives for oral or parenteral administration to human patients in a daily dosage of about 10–1000 mg/kg of body weight such as 3 g/day (cols. 10 and 20).

These patents similarly recognize the equivalency or interchangeability of nephrosis and nephritis as regards nephrotic syndrome and lupus nephritis as well as lupus nephrosis, and confirm that induced renal disease test results in animals such as rats are indicative of comparable results in human patients suffering from renal disease.

[19] U.S. Pat. No. 4,912,215, issued Mar. 27, 1990 to Yazawa et al, concerns production of a stated Q-1047 substance useful as a therapeutic agent for nephritis. Tests on PAN nephrosis rats using the Q-1047 substance show that while the PAN induced nephrosis rats had an increase in urinary protein level, those then given the Q-1047 substance did not, with consequent kidney tissue examination indicating that the rats given PAN alone showed degeneration and necrosis of glomerular capillary vessels, hypertrophy of endothelial cells, mesangial thickening due to hyperplasia of mesangial cells and deposition of hyaline droplet-like substance, whereas in rats also given the Q-1047 substance such changes or abnormalities were lesser in extent and lower in incidence (FIG. 35; cols. 9–10).

The Q-1047 substance may be formulated with excipients such as lactose, starch, etc. for oral administration, and with preservatives for non-oral administration, at an oral dose of about 0.1–100 mg/kg of body weight about 1–3 times daily, or in the form of an injection at a dose of 0.1–10 mg/kg.

This patent similarly recognizes the equivalency or interchangeability (per se) of nephrosis and nephritis, and confirms that induced renal disease test results in animals such as rats are indicative of comparable results in human patients suffering from renal disease.

[20] U.S. Pat. No. 5,182,266, issued Jan. 26, 1993 to Kleinert, concerns treating or inhibiting renal dysfunction (disease) such as chronic or acute renal failure in a human (or other mammal) by administering to the human a therapeutically effective amount of a known stated amino acid amide compound serving as renin inhibitor. It is stated that renal diseases are characterized by reduced renal blood flow, reduced glomerular filtration rate (GFR), proteinuria, hematuria and/or alterations in water and sodium excretion. It is also stated that the effect of a renin inhibitor on renal failure can be demonstrated by observing the effects on renal hemodynamics that can alter GFR of a renin inhibitor administered to animals in which acute renal failure has been modeled, for example ischemia, ureteral obstruction or nephrotoxic agents such as gentamicin, cis-platin and the like; and also that the effects of a renin inhibitor on chronic renal failure can be demonstrated by observing the effects on proteinuria, histopathologic improvement and long term stabilization of GFR of a renin inhibitor administered to animals in which chronic renal failure has been modeled, for example by reduced renal mass, puromycin-induced nephrosis or diabetic nephropathy (col. 45).

This patent sets forth the following background information (cols. 1-2).

Acute renal failure is noted as a condition characterized by an abrupt and sustained reduction in GFR occurring within a period of hours in response to an acute ischemic or nephrotoxic insult, which is not immediately reversible when the initial disturbance has been eliminated. Immediate improvement in GFR and increasing fluid flow through the nephron appears to be of critical importance in the prognosis of acute renal failure.

Chronic renal failure is noted as being characterized by (1) a reduction in GFR that has been evident for 3 to 6 months, (2) a continued decline in GFR over a period of years and (3) symptoms of uremia. The term renal insufficiency is often used to characterize a condition in which a mild reduction in GFR has occurred, but no uremic symptoms have appeared. Chronic renal failure denotes irreversible nephron loss, whereas acute renal failure reflects a reduction in single nephron GFR due to potentially reversible nephron injury.

It is noted that proteinuria (elevated urinary excretion of plasma proteins) can be present during acute and chronic renal failure and has been shown to be an accurate index of the extent of glomerular damage. Agents that reduce proteinuria have been shown to have beneficial effects on glomerular injury.

It is also noted that angiotensin II (A II) is believed to play a role in renal failure, A II being a peptide hormone produced in the kidney in a two step process, the first step of which is the cleavage of angiotensinogen by the enzyme renin. Renin is stored primarily in the juxtaglomerular cells of the kidney. It is further noted that A II has profound effects on the kidney, including direct vasoconstriction of the renal vascular bed thereby altering renal blood flow, stimulation of sodium resorption, modification of glomerular feedback, alteration of GFR through changes either in the hydraulic pressure or by reducing the filtration surface area secondary to mesangial cell contraction, and increasing distal nephron sodium resorption indirectly through stimulation of aldosterone secretion. A II increases the passage of circulation macromolecules into the glomerular mesangium and decreases their egress. All these effects of A II have a negative impact on renal disease, whereby an agent that prevents or inhibits formation of A II, such as a renin inhibitor, can have a beneficial effect on renal disease.

The renin inhibitor may be formulated with vehicles and solvents such as water, dextrose solution, mannitol solution, Ringer's solution and isotonic chloride solution, or solids such as sucrose, lactose or starch at a daily dosage of about 0.001-10 mg/kg of body weight (cols. 45-46).

This patent confirms that induced nephrosis modeling results are indicative of comparable results in human patients suffering from renal disease.

The following patents and publications [21] to [28] relate to use of N-acetylneuraminic acid (NANA):

[21] U.S. Pat. No. 4,410,515, issued Oct. 18, 1983 to Horlick et al; [22] U.S. Pat. No. 4,521,410, issued Jun. 4, 1985 to Horlick et al; and [23] U.S. Pat. No. 4,661,294, issued Apr. 28, 1987 to Horlick et al; commonly concern methods of treating calcium and phosphorus metabolic disorders in an animal, especially humans, i.e. in a mammal, by administering thereto in an amount sufficient to regulate calcium and phosphorous homeostasis therein of a stated water soluble vitamin D type compound including a glycosidic residue therein such as an N-acetylneuraminic acid (NANA) residue. Tests on rats and on human fibroblasts with said compound confirm the efficacy of the treatment methods.

[24] U.S. Pat. No. 4,698,332, issued Oct. 6, 1987 to Ogasawara et al (of common assignee herewith) concerns promoting expectoration by administering to a human being by inhalation, an effective amount of NANA or a pharmaceutically active salt thereof, which as an expectorant acts on the theological properties of sputum and directly promotes ciliary motion in the airway for removing the sputum. Tests using cilium cells from the human airway and cilia of frog palatine mucosa before and after application of NANA or its salt confirm the efficacy of the method as sufficient for treating human patients.

[25] U.S. Pat. No. 5,177,062, issued Jan. 5, 1993 to Miyata et al (of overlapping inventorship and common assignee herewith) concerns treating immune complex (antigen-antibody complex) diseases characterized by an Arthus type inflammatory response in an animal, by administering to the animal, e.g. by injection, a preparation having an effective amount of NANA or a salt thereof. It is stated that the Arthus reaction is an inflammation reaction which can be observed on the skin as edema and bleeding. Tests are set forth using NANA or its salts on guinea pigs for passive cutaneous Anaphylaxis reaction for determining inhibition of type I allergy; for determining inhibition of histamine increase due to bronchial anaphylaxis; and for Passive Arthus reaction for determining inhibition of skin bleeding; and on rats for determining inhibition of leukotriene level increase due to sulfate gas exposure.

[26] European Pat. Application No. 296,620 (EP-A 296,620), published Dec. 28, 1988, which is analogous to said [24] U.S. Pat. No. 4,698,332, concerns treating a human or animal living body by spraying the nostrils with NANA or a salt thereof for relieving nasal obstruction symptoms of a mucous membrane, with tests on rats and on human fibroblasts using NANA or its salt confirming the efficacy of the method as sufficient for treating human patients.

[27] European Pat. Application No. 386,657 (EP-A 386,657), published Sep. 12, 1990, generally corresponds to said [25] U.S. Pat. No. 5,177,062.

[28] Japanese Pat. Application Publication No. JP 1,299,294 (JP-A 1,299,294), published Dec. 4, 1989 (English abstract), concerns use of NANA as a starting material in a process for producing an anhydro derivative thereof serving as a new anti vital, anti nephritic and anti dement agent.

The inventors have found an inhibitory effect of N-acetylneuraminic acid on renal disease such as nephrosis, i.e. nephrotic syndrome, and particularly glomerular nephrosis, which action had not been known, leading to the present invention.

The anti vital, anti inflammatory and anti allergic actions of N-acetylneuraminic acid noted in said articles [1] to [4], and its expectoration promoting, immune complex disease inflammatory response, and nasal obstruction relieving, actions noted in said patents [24] and [25] and publication [26], are completely unrelated to its therapeutic effectiveness according to the invention on nephrosis in the field of renal disease as contemplated in said articles [5] to [10] and patents [11] to [20].

SUMMARY OF THE INVENTION

An object of the invention is to provide a preparation for treating renal disease, containing N-acetylneuraminic acid as an effective ingredient.

A preparation for treating renal disease according to the invention contains, as an effective ingredient, N-acetylneuraminic acid shown by the following formula:

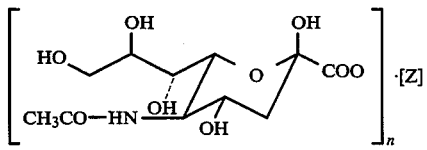

wherein, at n=1, Z represents hydrogen, lithium, potassium, sodium, ammonium or organic ammonium, and at n=2, Z represents calcium, barium or magnesium, or a salt of N-acetylneuraminic acid.

The preparation according to the invention may contain a pharmacologically acceptable carrier such as physiological saline solution, stabilizers or preservatives.

The preparation may be administered intraperitoneally, subcutaneously or intravenously by injection.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter and examples in which preferred embodiments of the invention are illustrated.

Specifically, the inhibitory effect of the N-acetylneuraminic acid or salt compound of the above formula on nephritis, i.e. nephrosis or nephrotic syndrome, is explained by way of the following examples, referring to the attached drawings.

DETAILED DESCRIPTION OF THE INVENTION

This invention concerns the discovery that the N-acetylneuraminic acid compounds (NANA) of the above formula, i.e. the acid and its alkali metal, ammonium and alkaline earth metal type salts, possess an inhibiting effect on nephrosis (nephritis, nephrotic syndrome), and specifically glomerular nephrosis, as exemplified by their ability to reverse the classic nephrosis (nephritis) effect induced by administration to mammalian subjects of puromycin aminonucleoside (PAN).

The invention relates in particular to a method of treating nephrotic syndrome in a subject, such as a human being or other animal exhibiting a nephrotic syndrome condition, comprising administering to the subject a nephrotic syndrome inhibiting effective amount of an N-acetylneuraminic acid compound of the above formula, such as by intraperitoneal, subcutaneous or intravenous injection, for example in the form of a therapeutic preparation of said compound with a pharmacologically acceptable carrier such as physiological saline solution or water.

More specifically, a method of treating a nephrotic syndrome condition corresponding to the symptoms induced by administration of puromycin aminonucleoside (PAN) is contemplated, comprising administering to a human being or other animal subject exhibiting such condition a nephrotic syndrome inhibiting effective amount of said compound, such as by injection, for example in the form of a said therapeutic preparation.

The following examples are set forth by way of illustration and not limitation of the invention. All parts referred to therein are parts by weight unless specifically stated otherwise.

EXAMPLE 1

Effect on Puromycin aminonucleoside (PAN) induced nephritis, i.e. PAN induced nephrosis or nephrotic syndrome:

(1) Experimental animals

Male Sprague-Dawley (SD) rats weighing 160–180 g were used.

(2) Materials

As the nephritis, i.e. nephrosis or nephrotic syndrome, causing substance, PAN (made by Sigma Co., Ltd.) was used. As the test compound, sodium N-acetylneuraminate (made by MECT Corporation) was used.

(3) Methods

PAN was intraperitoneally administered in an amount of 80 mg per 1 kg of body weight to rats to cause nephritis, i.e. nephrosis or nephrotic syndrome. Then, the test compound (Groups I, II or III) or physiological saline solution (Group IV) was intraperitoneally administered 3 times a day (morning, noon and evening) for 14 consecutive days immediately after treatment with PAN as follows. As a positive control, methylprednisolone was subcutaneously administered to rats of Group V once a day (noon) for 14 consecutive days immediately after treatment with PAN. Moreover, 3, 6, 9 and 13 days after treatment with PAN, 5 ml water was loaded, and the urine was collected for 6 hours. Fourteen days after treatment with PAN, autopsies were made, the kidneys were extirpated and their moist weights were measured.

Group I: 0.1 mg Sodium N-acetylneuraminate per 1 kg of body weight was administered.

Group II: 0.5 mg Sodium N-acetylneuraminate per 1 kg of body weight was administered.

Group III: 1.0 mg Sodium N-acetylneuraminate per 1 kg of body weight was administered.

Group IV: 2.5 ml Physiological saline solution per 1 kg of body weight was administered.

Group V: 2 mg Methylprednisolone per 1 kg of body weight was administered.

Group VI: Normal rats (no drug was given).

(4) Results

[1] The weight gain rates and the moist kidney weights in Group I–VI are shown in Table 1.

TABLE 1

| Experimental Group | Number of Rats | Weight Gain Rate (%) | Kidney Moist Weight (g/100 g) |
|---|---|---|---|
| I (Sodium N-acetylneuraminate 0.1 mg/kg) | 10 | 127.1 ± 2.0 | 0.47 ± 0.02 |
| II (Sodium N-acetylneuraminate 0.5 mg/kg) | 10 | 128.4 ± 1.8 | 0.44 ± 0.02 |
| III (Sodium N-acetylneuraminate 1.0 mg/kg) | 10 | 131.3 ± 1.9 | 0.42 ± 0.02 |
| IV (Physiological saline solution) | 10 | 118.1 ± 1.6 | 0.48 ± 0.01 |
| V (Methylprednisolone | 10 | 107.7 ± 1.6 | 0.43 ± 0.01 |

TABLE 1-continued

| Experimental Group | Number of Rats | Weight Gain Rate (%) | Kidney Moist Weight (g/100 g) |
|---|---|---|---|
| 2.0 mg/kg) | | | |
| VI (Normal animals) | 10 | 134.7 ± 2.8 | 0.37 ± 0.01 |

Although weight gain was inhibited by administration of PAN (Group IV), the groups treated with sodium N-acetylneuraminate showed dose-dependent prevention against inhibition of weight gain and an improvement in systemic symptoms (Groups I-III). In addition, kidney moist weight was increased after administration of PAN (Group IV), while the increase was dose-dependently inhibited in the groups treated with sodium N-acetylneuraminate (Groups I-III). Also, in the group given methylprednisolone as a positive control (Group V), similar inhibitory effect was observed. [2] The urinary protein contents on the 3rd, 6th, 9th and 13th day in Groups I-VI are shown in Table 2.

Acute toxicity tests of sodium N-acetylneuraminate in mice, rats and guinea pigs by oral administration, subcutaneous injection, intraperitoneal injection, intravenous injection and inhalation were performed as follows.

(1) Experimental animals

| ICR mice | 6 weeks of age |
|---|---|
| SD rats | 6 weeks of age |
| Harley guinea pigs | 6 weeks of age |

(2) Drug concentration
20% (w/v) - dissolved in distilled water
(3) The number of animals at each level
10 mice, rats or guinea pigs
(4) Period of observation
14 days
(5) Calculation of $LD_{50}$
Probit method
The results are shown in Table 3.

TABLE 3

Acute toxicity test of sodium N-acetylneuraminate

| | | $LD_{50}$ (mg/kg) Administering Route | | | | |
|---|---|---|---|---|---|---|
| Species | Sex | Oral | Subcutaneous | Intraperitonial | Intravenous | Inhalation |
| Mice | Male | >5,000 | >5,000 | >5,000 | >5,000 | — |
| | Female | >5,000 | >5,000 | >5,000 | >5,000 | — |
| Rats | Male | >5,000 | >5,000 | >5,000 | >5,000 | >4,000 mg/m$^3$ |
| | Female | >5,000 | >5,000 | >5,000 | >5,000 | >4,000 mg/m$^3$ |
| Guinea pigs | | — | — | — | >5,000 | — |

— Inhalation was carried out by spraying the nebulized test compound for one hour.

TABLE 2

| Experimental Group | Number of Rats | Urinary Protein Content (mg/24 hours) | | | |
|---|---|---|---|---|---|
| | | 3rd Day | 6th Day | 9th Day | 13th Day |
| I (Sodium N-acetylneuraminate 0.1 mg/kg) | 10 | 14.1 ± 1.1 | 83.4 ± 8.6 | 99.6 ± 14.2 | 109.9 ± 12.9 |
| II (Sodium N-acetylneuraminate 0.5 mg/kg) | 10 | 11.3 ± 0.8 | 49.1 ± 13.6 | 59.9 ± 14.7 | 94.5 ± 30.4 |
| III (Sodium N-acetylneuraminate 1.0 mg/kg) | 10 | 5.1 ± 0.4 | 50.5 ± 10.7 | 51.2 ± 15.6 | 77.9 ± 17.9 |
| IV (Physiological- saline solution) | 10 | 9.5 ± 2.1 | 109.5 ± 17.7 | 145.9 ± 29.1 | 236.4 ± 43.6 |
| V (Methylpredni- solone 2.0 mg/kg) | 10 | 22.3 ± 2.1 | 55.8 ± 11.4 | 68.7 ± 13.1 | 56.1 ± 12.5 |
| VI (Normal animals) | 10 | 6.5 ± 1.7 | 11.3 ± 0.3 | 15.7 ± 2.5 | 16.3 ± 1.7 |

Administration of PAN increased the urinary protein content from the 6th day (Group IV), while in the groups given sodium N-acetylneuraminate (Groups I-III), increases in the urinary protein contents were dose-dependently inhibited on the 6th, 9th and 13th day. The group given methylprednisolone as a positive control (Group V) also showed similar inhibitory effect.

(5) Judgement

The above mentioned results on PAN-induced nephritis, i.e. PAN-induced nephrosis (nephrotic syndrome) indicate that sodium N-acetylneuraminate has a therapeutic effect on renal disease, i.e. on nephrosis or nephrotic syndrome.

EXAMPLE 2

Acute toxicity test:

EXAMPLE 3

Simplified acute toxicity test:

A simplified acute toxicity test of N-acetylneuraminates in mice by intravenous injection was carried out as follows.

(1) Test compounds
Lithium-, potassium-, barium- and magnesium- salts of N-acetylneuraminic acid were used (all were from MECT Corporation).
(2) Experimental animals
Male ddy mice
Body weights at the start of the test: 17.7–21.1 g
The number of animals at each level: 3 mice
(3) Room temperature: 23±1° C. - Humidity: 55±7%
(4) Administering route Vein (5) Administering method and doses The above-mentioned test compounds were dissolved in physiological saline solution to make a 0.2 ml solution per 20 g of body weight in a mouse as an injection fluid and injected into the tail vein. The doses were 500, 1,000 and 2,000 mg/kg.

(6) Observation on general symptoms and deaths

Presence or absence of general symptoms and deaths were observed for 7 days immediately after administration.

(7) Lethality

The lethalities are shown in Table 4.

TABLE 4

| Drug | Dose mg/kg | The number of deaths per day course | | | | |
|---|---|---|---|---|---|---|
| | | 1 3 6 | 24 hrs | 2 3 4 5 6 | 7 days | Final Lethality |
| Lithium | 500 | 0 0 0 | 0 | 0 0 0 0 0 | 0 | 0/3 |
| N-acetyl- | 1000 | 0 0 0 | 0 | 0 0 0 0 0 | 0 | 0/3 |
| neuraminate | 2000 | 0 0 0 | 0 | 0 0 0 0 0 | 0 | 0/3 |
| Potassium | 500 | 0 0 0 | 0 | 0 0 0 0 0 | 0 | 0/3 |
| N-acetyl- | 1000 | 3 0 0 | 0 | 0 0 0 0 0 | 0 | 3/3 |
| neuraminate | 2000 | 3 0 0 | 0 | 0 0 0 0 0 | 0 | 3/3 |
| Barium | 500 | 3 0 0 | 0 | 0 0 0 0 0 | 0 | 3/3 |
| N-acetyl- | 1000 | 3 0 0 | 0 | 0 0 0 0 0 | 0 | 3/3 |
| neuraminate | 2000 | 3 0 0 | 0 | 0 0 0 0 0 | 0 | 3/3 |
| Magnesium | 500 | 0 0 0 | 0 | 0 0 0 0 0 | 0 | 0/3 |
| N-acetyl- | 1000 | 3 0 0 | 0 | 0 0 0 0 0 | 0 | 3/3 |
| neuraminate | 2000 | 3 0 0 | 0 | 0 0 0 0 0 | 0 | 3/3 |

At the doses of 1,000 and 2,000 mg/kg, all of the 3 mice died in the groups treated with magnesium-, barium- and potassium- N-acetylneuraminates. At the dose of 500 mg/kg, all 3 of the 3 mice in the group given barium N-acetylneuraminate died. There were no deaths in any other group.

(8) General symptoms

The death followed clonic convulsion and incontinence of urine and most of the animals died immediately or within one minute after injection. In a few survivors, inhibition of spontaneous movement was observed, which was normalized within one hour.

As mentioned above, N-acetylneuraminic acid has an inhibitory effect on nephritis, i.e nephrosis or nephrotic syndrome, and is a useful compound as a therapeutic for renal disease.

While the mechanism of action is not yet fully understood, it is considered that administration of said N-acetylneuraminic acid compound (NANA) restores the impaired charge barrier of the glomerular base membrane (GBM). Since PAN nephrosis in rats, as earlier noted, is a very good and art recognized model of glomerular nephrosis (nephritis), the data in the above Examples resulting from experiments using rats are considered applicable to human glomerular nephrosis (nephritis, nephrotic syndrome) regarding the unexpected inhibiting effect thereon of said N-acetylneuraminic acid compound according to the invention.

Rat and other non-human animal (mammal) tests of the given type serve as acceptable models of corresponding action in humans, being art recognized as reliable predictors of effective treatment of nephrosis, i.e. nephrotic syndrome, in human hosts, as demonstrated by the above discussed prior art.

The amount of the NANA compound administered will vary depending on the inhibiting effect of the particular species compound (e.g. the acid or a given salt) employed, mode of administration, severity of the renal disease symptoms and other known factors. Typically, the NANA compound may be used for human patients at a daily dosage of about 1 to 1000 mg/kg of body weight.

It is especially used as an injectable therapeutic preparation with a conventional pharmacologically acceptable carrier such as is detailed in the above discussed prior art. In particular, besides physiological saline (i.e. normal saline solution, 0.9% NaCl in water) and water, other such carriers are ethanol, vegetable oil, and the like.

Regarding the results of therapeutic effect for treating renal disease (nephrotic syndrome) of the given NANA compound per Example 1 above, it will be appreciated that the test compound sodium N-acetylneuraminate (Groups I, II and III) was dissolved in physiological saline and intraperitoneally administered, compared to intraperitoneal administration of physiological saline alone (Group IV) and subcutaneous administration of methylprednisolone (Group V).

As to weight gain, which is used as an index of systemic effect, it is clear from Table 1 that methylprednisolone shows a greater inhibition of weight gain, which means that it has a greater systemic side effect, compared to sodium N-acetylneuraminate which does not show such side effect but instead prevents inhibition of weight gain induced by PAN administration and improves systemic symptoms.

As to kidney moist weight, which is an index of edema of the kidney, it is clear from Table 1 that the test compound sodium N-acetylneuraminate, like prednisolone, inhibits increase in kidney moist weight and thus inhibits kidney edema.

As to urinary protein content, which is indicative of the presence or absence of proteinuria (excess protein in urine), proteinuria being a symptom of PAN-induced nephrosis, it is clear from Table 2 that the test compound sodium N-acetylneuraminate, like methylprednisolone, inhibits increase in urinary protein content. Such inhibition of urinary protein content is indicative of the therapeutic effect on nephrosis of the given NANA compound.

The above noted therapeutic effect for treating renal disease (nephrotic syndrome) is similarly achievable using as the NANA compound the free acid (n=1, Z=hydrogen) or a different salt (n=1, Z=lithium, potassium, ammonium or organic ammonium; n=2, Z=calcium, barium or magnesium). The organic ammonium salts are those of the usual organic ammonium groups such as cyclic and linear (non-cyclic) organic ammonium ions, including corresponding hydrocarbon substituted ammonium ions, e.g. having alkyl, especially lower alkyl such as alkyl having 1–4 carbon atoms, phenyl and/or benzyl as hydrocarbon substituents, with the organic ammonium group having a hydrogen atom attached to the ammonium nitrogen atom, e.g. N-heterocyclic ammonium ions derived from pyridine, piperidine, pyrroline (dihydropyrrole), morpholine, etc., such hydrocarbon group substituted N-heterocyclic ammonium ions, and linear (non-heterocyclic) ammonium ions such as $(R_1)(R_2)(R_3)NH^+$ wherein $R_1$, $R_2$ and $R_3$, which may be the same or different hydrocarbon substituents, are alkyl, e.g. lower alkyl, and particularly alkyl having 1–4 carbon atoms, phenyl or benzyl.

While specific embodiments of the invention have been shown and described in detail to illustrate the application of the principles of the invention, it will be understood that the invention may be embodied otherwise without departing from such principles.

What is claimed is:

1. Method of treating nephrotic syndrome in a subject exhibiting a nephrotic syndrome condition, comprising administering thereto a nephrotic syndrome inhibiting effective amount of an N-acetylneuraminic acid compound of the formula

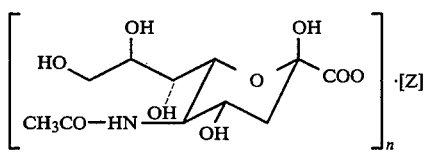

wherein n is 1 and Z represents sodium.

2. Method of claim 1 wherein the compound is administered in the form of a therapeutic preparation thereof with a pharmacologically acceptable carrier.

3. Method of claim 2 wherein the carrier is physiological saline solution or water.

4. Method of claim 2 wherein the administration is by injection.

5. Method of treating a nephrotic syndrome condition corresponding to the symptoms induced by administration of puromycin aminonucleoside, comprising administering to a subject exhibiting such condition a therapeutic preparation which comprises a nephrotic syndrome inhibiting effective amount of an N-acetylneuraminic acid compound of the formula

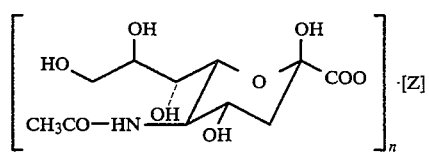

wherein n is 1 and Z represents sodium, and a pharmacologically acceptable carrier.

6. Method of claim 5 wherein the carrier is physiological saline solution or water.

7. Method of claim 5 wherein the administration is by injection.

* * * * *